(12) United States Patent
Scherich

(10) Patent No.: US 11,707,601 B2
(45) Date of Patent: Jul. 25, 2023

(54) COVER TO FACILITATE REDUCED-TOUCH INSERTION OF A CATHETER AND RELATED SYSTEMS AND METHODS

(71) Applicant: Becton, Dickinson and Company, Franklin Lakes, NJ (US)

(72) Inventor: Megan Scherich, Salt Lake City, UT (US)

(73) Assignee: Becton, Dickinson and Company, Franklin Lakes, NJ (US)

(*) Notice: Subject to any disclaimer, the term of this patent is extended or adjusted under 35 U.S.C. 154(b) by 220 days.

(21) Appl. No.: 17/166,886

(22) Filed: Feb. 3, 2021

(65) Prior Publication Data

US 2021/0260338 A1 Aug. 26, 2021

Related U.S. Application Data

(60) Provisional application No. 62/980,832, filed on Feb. 24, 2020.

(51) Int. Cl.
| | |
|---|---|
| *A61M 25/01* | (2006.01) |
| *A61M 25/06* | (2006.01) |
| *A61M 25/00* | (2006.01) |
| *A61M 5/32* | (2006.01) |

(52) U.S. Cl.
CPC ..... *A61M 25/0111* (2013.01); *A61M 25/0097* (2013.01); *A61M 25/0606* (2013.01); *A61M 5/3232* (2013.01); *A61M 2205/276* (2013.01)

(58) Field of Classification Search
CPC .......... A61M 25/0111; A61M 25/0097; A61M 25/0606; A61M 25/06; A61M 25/0612; A61M 2025/0681; A61M 25/0631; A61M 2205/276; A61M 5/3232; A61M 5/322; A61M 25/0618; A61M 25/0625
See application file for complete search history.

(56) References Cited

U.S. PATENT DOCUMENTS

| | | | | |
|---|---|---|---|---|
| 3,672,367 | A | * | 6/1972 | Scislowicz ......... A61M 25/0111 604/163 |
| 5,051,109 | A | * | 9/1991 | Simon ................. A61M 5/3273 604/263 |
| 5,423,766 | A | * | 6/1995 | Di Cesare .......... A61M 5/3275 604/263 |

(Continued)

*Primary Examiner* — Katherine H Schwiker
*Assistant Examiner* — Robert F Allen
(74) *Attorney, Agent, or Firm* — Kirton McConkie; Whitney Blair; Kevin Stinger

(57) ABSTRACT

A catheter system may include a catheter assembly and a needle assembly. The catheter assembly may include a catheter hub and a catheter extending distally from the distal end of the catheter hub. The catheter assembly may include a cover coupled to a proximal portion of the catheter hub. The cover may be configured to reduce contact with the catheter assembly during initial insertion of the catheter assembly into vasculature of a patient and/or threading the catheter, which may reduce a risk of bacterial contamination of the catheter. The needle assembly may include an introducer needle, a housing, and a needle hub disposed within the housing. The housing may include a button. A proximal end of the introducer needle may be secured within the needle hub. In response to activation of the button, the needle hub and the introducer needle may move proximally within the housing.

18 Claims, 7 Drawing Sheets

(56) References Cited

U.S. PATENT DOCUMENTS

| | | | |
|---|---|---|---|
| 5,501,675 A | 3/1996 | Erskine | |
| 5,584,818 A * | 12/1996 | Morrison | A61M 5/3275 |
| | | | 604/110 |
| 5,713,876 A * | 2/1998 | Bogert | A61M 25/0631 |
| | | | 604/243 |
| 5,853,393 A * | 12/1998 | Bogert | A61M 25/0631 |
| | | | 604/165.02 |
| 5,910,132 A * | 6/1999 | Schultz | A61M 5/3275 |
| | | | 604/162 |
| 6,090,078 A * | 7/2000 | Erskine | A61M 25/0631 |
| | | | 604/230 |
| 7,344,516 B2 * | 3/2008 | Erskine | A61M 5/3269 |
| | | | 604/110 |
| 2017/0028172 A1 * | 2/2017 | Ishida | A61M 25/0612 |
| 2017/0049994 A1 * | 2/2017 | Truhler | A61M 25/0136 |
| 2018/0280626 A1 * | 10/2018 | Branson | A61M 25/0606 |

\* cited by examiner

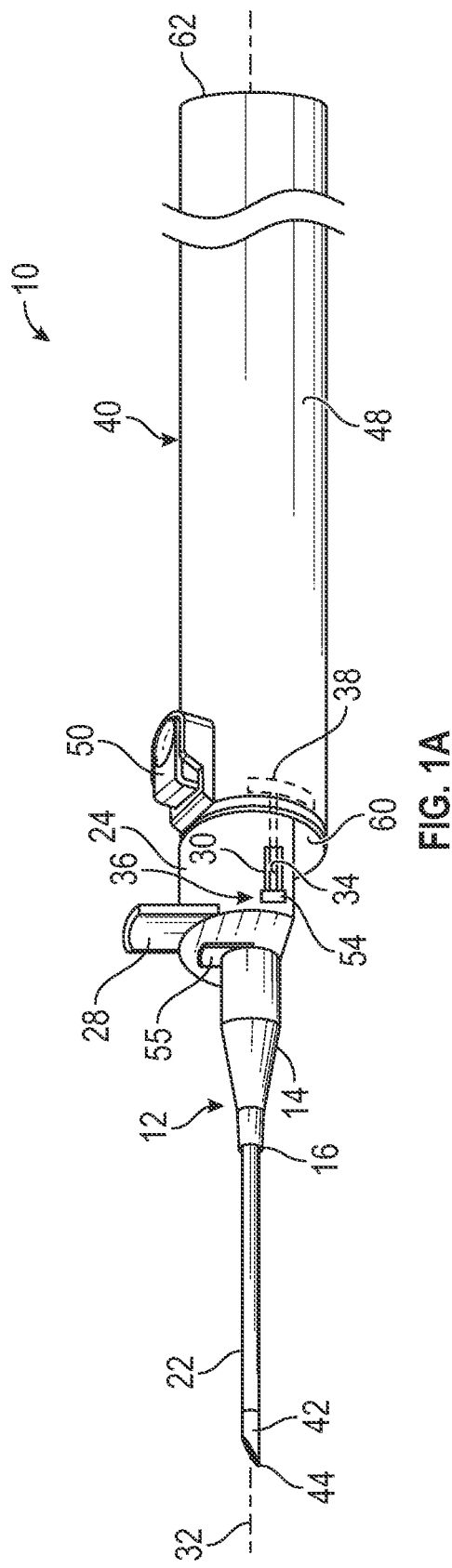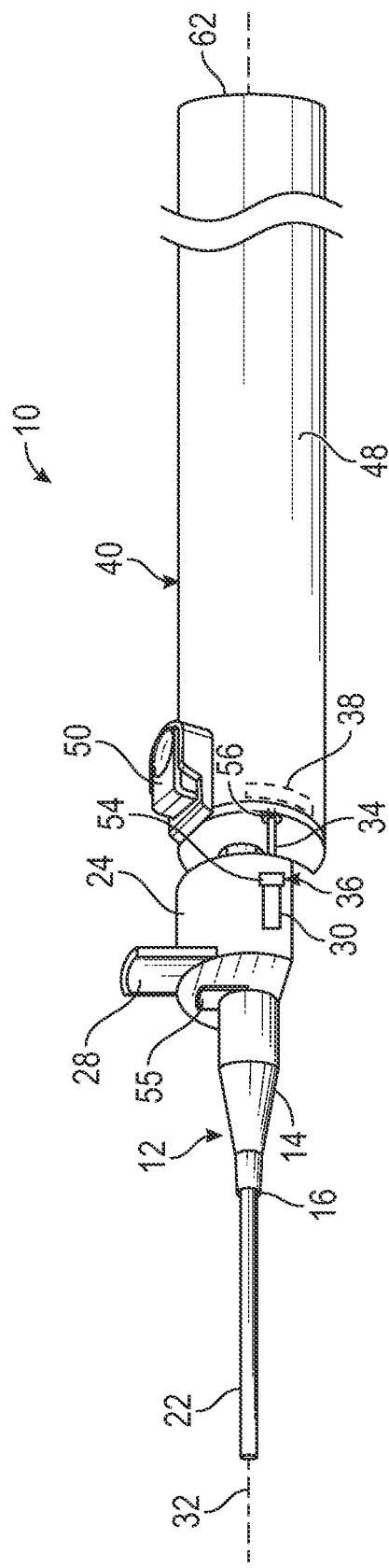

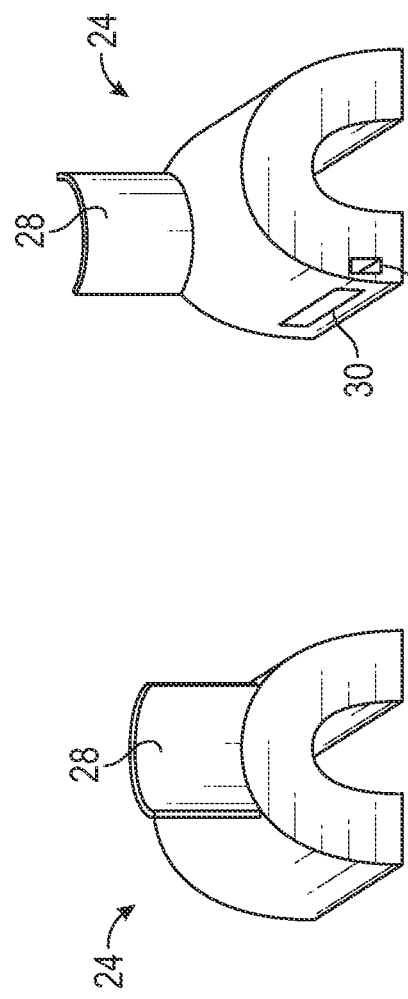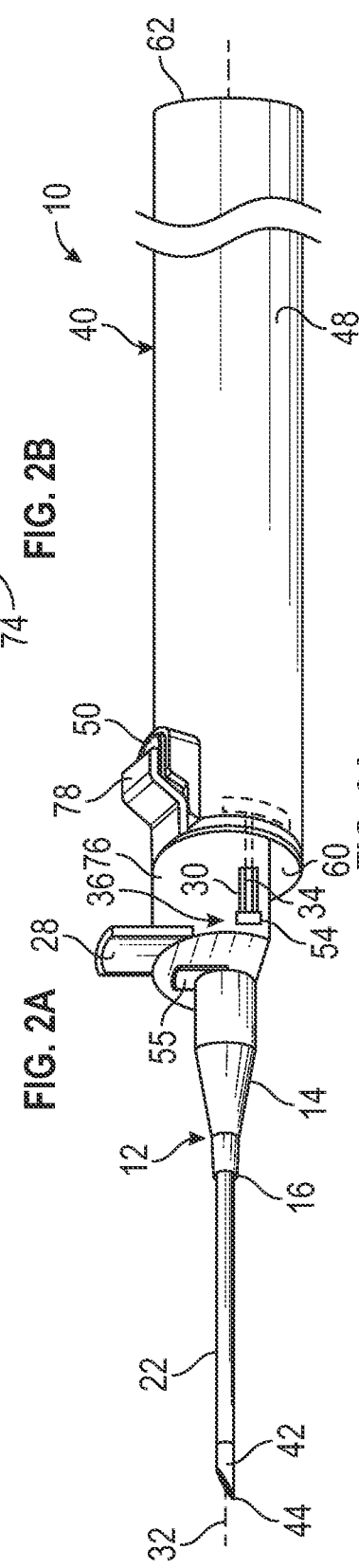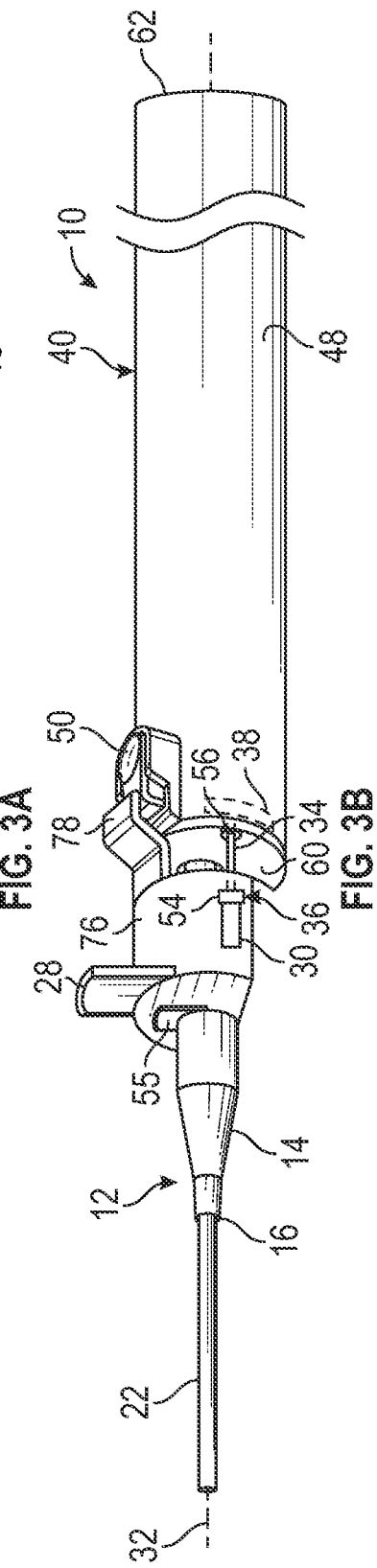

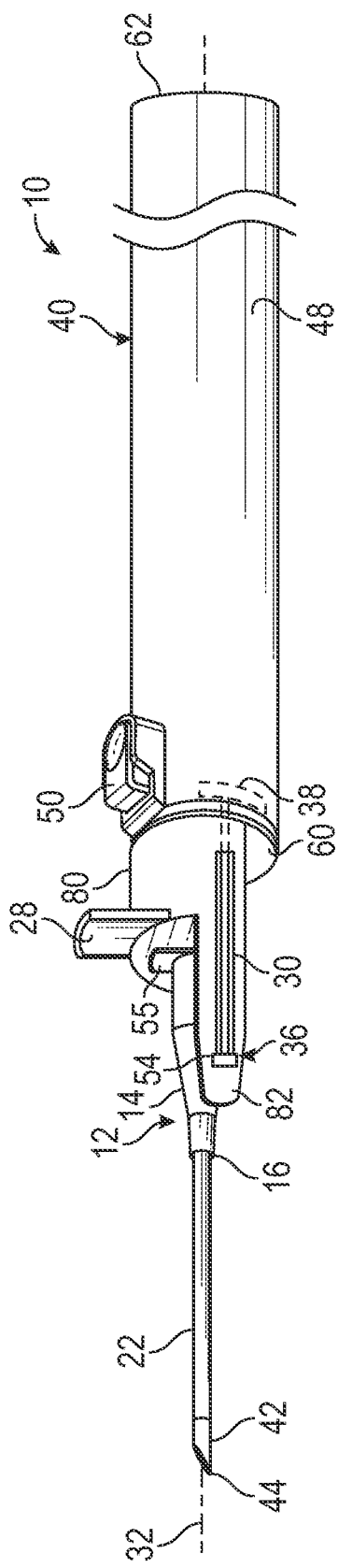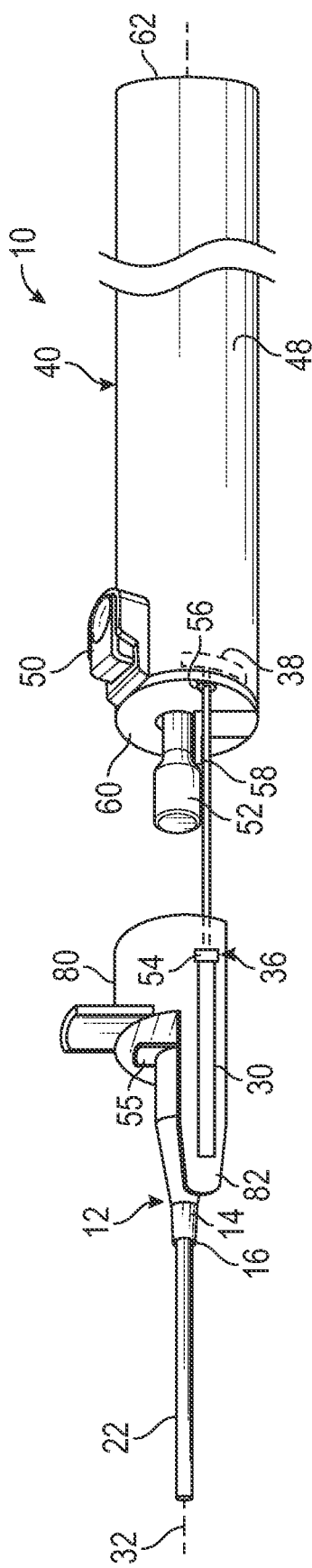

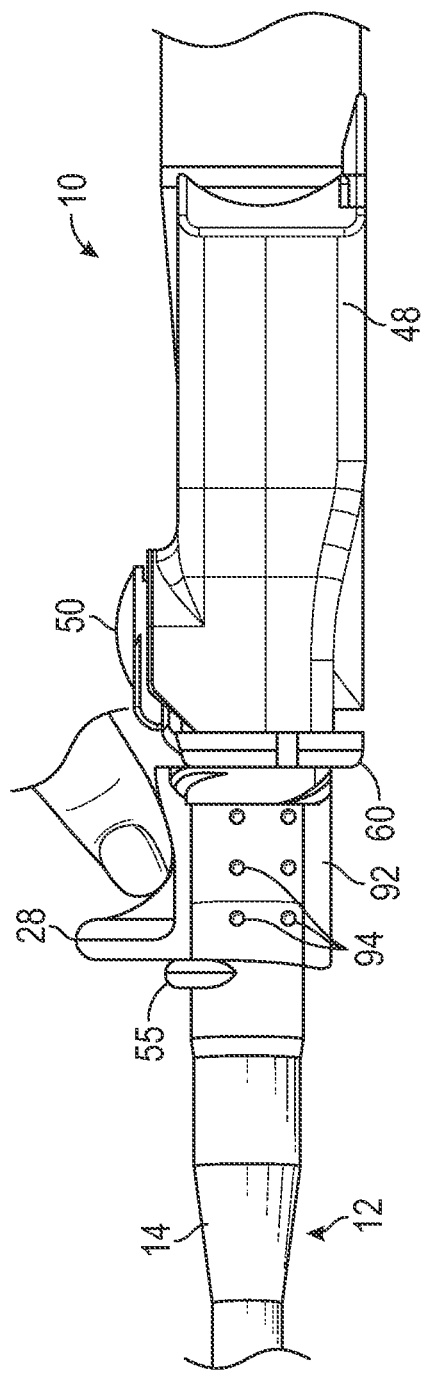
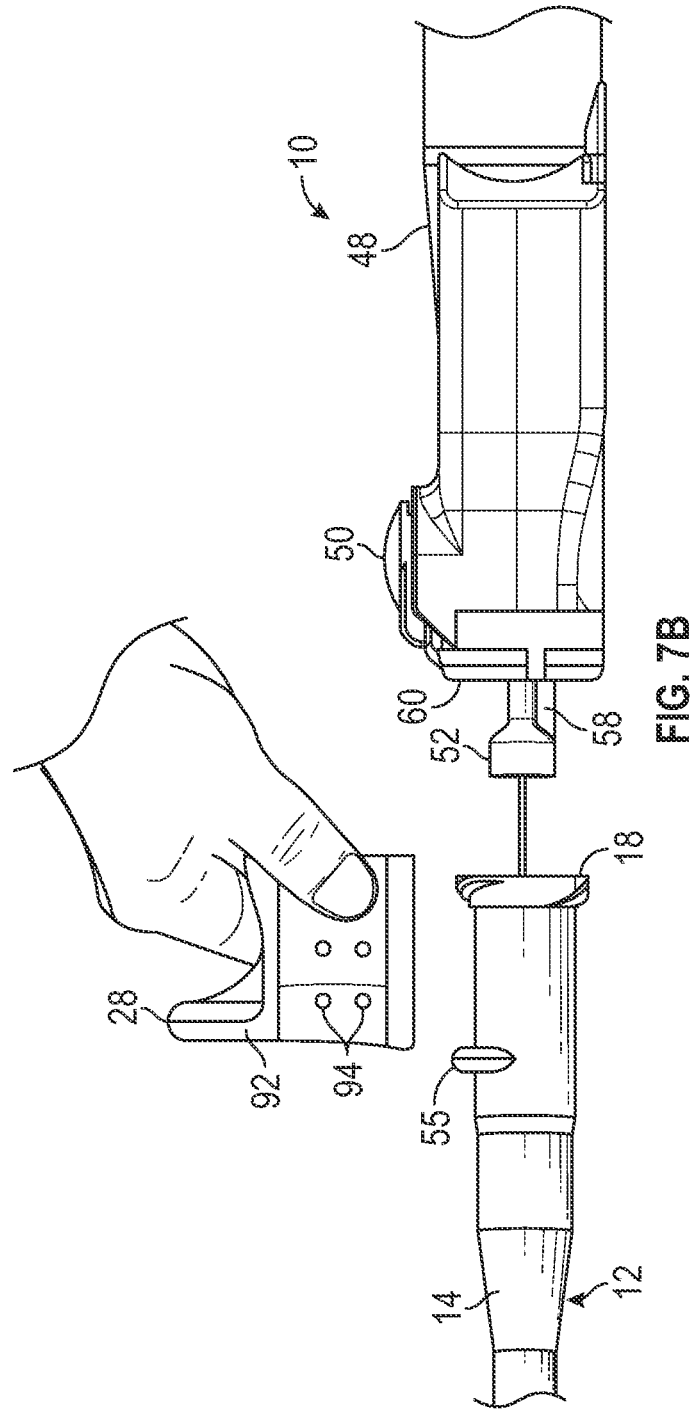

COVER TO FACILITATE REDUCED-TOUCH INSERTION OF A CATHETER AND RELATED SYSTEMS AND METHODS

RELATED APPLICATIONS

This application claims the benefit of U.S. Provisional Patent Application No. 62/980,832, filed on Feb. 24, 2020, entitled "COVER TO FACILITATE REDUCED-TOUCH INSERTION OF A CATHETER AND RELATED SYSTEMS AND METHODS," which is incorporated herein in its entirety.

BACKGROUND

Catheters are commonly used for a variety of infusion therapies. For example, catheters may be used for infusing fluids, such as normal saline solution, various medicaments, and total parenteral nutrition, into a patient. Catheters may also be used for withdrawing blood from the patient.

A common type of catheter is an over-the-needle peripheral intravenous ("IV") catheter. As its name implies, the over-the-needle catheter may be mounted over an introducer needle having a sharp distal tip. A catheter assembly may include a catheter hub, the catheter extending distally from the catheter hub, and the introducer needle extending through the catheter. The catheter and the introducer needle may be assembled so that the distal tip of the introducer needle extends beyond the distal tip of the catheter with the bevel of the needle facing up away from skin of the patient. The catheter and introducer needle are generally inserted at a shallow angle through the skin into vasculature of the patient.

In order to verify proper placement of the introducer needle and/or the catheter in the blood vessel, a user generally confirms that there is "flashback" of blood in a flashback chamber of the catheter assembly. Once placement of the needle has been confirmed, the user may temporarily occlude flow in the vasculature and remove the needle, leaving the catheter in place for future blood withdrawal or fluid infusion.

During insertion of the catheter into the vasculature of the patient, the user contacts and pushes on the catheter hub, which may contaminate the catheter hub with bacteria and lead to bacterial contamination of the catheter. Bacterial contamination of the catheter may increase a risk of hospital-acquired infection by the patient.

The subject matter claimed herein is not limited to embodiments that solve any disadvantages or that operate only in environments such as those described above. Rather, this background is only provided to illustrate one example technology area where some implementations described herein may be practiced.

SUMMARY

The present disclosure relates generally to a vascular access system, as well as related devices and methods. More specifically, in some embodiments, the present disclosure relates to a cover for a catheter hub of a catheter assembly. In some embodiments, a user may grip the cover instead of the catheter hub during insertion of a catheter into vasculature of a patient, which may reduce a risk of bacterial contamination of the catheter and/or hospital-acquired infection. In some embodiments, the cover may facilitate "no-touch" insertion of the catheter or insertion of the catheter without touching of the catheter hub by the user.

In some embodiments, a catheter system may include the catheter assembly. In some embodiments, the catheter assembly may include a catheter hub, which may include a distal end, a proximal end, and a lumen extending through the distal end of the catheter hub and the proximal end of the catheter hub. In some embodiments, the catheter assembly may include a catheter extending distally from the distal end of the catheter hub.

In some embodiments, the catheter system may include the cover, which may be coupled to a proximal portion of the catheter hub. In some embodiments, the cover may include a push tab and/or a slot. In some embodiments, the slot may extend parallel to a longitudinal axis of the catheter system. In some embodiments, the catheter system may include an extension, which may include a distal end and a proximal end. In some embodiments, the distal end of the extension may be slidable with respect to the slot.

In some embodiments, the catheter system may include a needle assembly, which may include an introducer needle. In some embodiments, the introducer needle may include a distal tip and a proximal end. In some embodiments, the needle assembly may include a housing, which may include an active safety mechanism. In some embodiments, the active safety mechanism may include a button. In some embodiments, the needle assembly may include a needle hub disposed within the housing. In some embodiments, the proximal end of the introducer needle may be secured within the needle hub. In some embodiments, the proximal end of the extension may be coupled to the needle hub.

In some embodiments, in response to activation of the button, the cover may be pulled proximally and removed from the proximal portion of the catheter hub. In some embodiments, the extension may include a tether. In some embodiments, the extension may include a spring. In some embodiments, in response to activation of the button, the needle hub may move proximally within the housing and a portion of the introducer needle may be disposed within the housing. In some embodiments, in response to release of the cover by the user, the spring may contract and the cover may move proximate the housing and shield the distal tip of the introducer needle. In some embodiments, the extension may be rigid.

In some embodiments, the cover may include a proximal extension covering at least a portion of the button to prevent premature activation of the button. In some embodiments, an outer surface of the cover may include one or more protrusions to facilitate gripping of the cover by a user. In some embodiments, the catheter hub may include a push tab. In some embodiments, a distal end of the cover may be proximate the push tab. In some embodiments, a distal end of the cover may include an arm, which may extend distally along a side of the catheter hub. In some embodiments, the arm may include a portion of the slot.

In some embodiments, a method may include inserting the catheter system into the vasculature of the patient. In some embodiments, the method may include threading the catheter, which may include contacting and applying a force in a distal direction to the cover to advance the catheter in the distal direction with respect to the introducer needle. In some embodiments, the extension may include the spring, and in response to activation of the button, a portion of the introducer needle may be disposed within the housing. In these and other embodiments, the method may include releasing the cover. In some embodiments, in response to release of the cover, the cover may move proximate the housing and shield the distal tip of the introducer needle. In some embodiments, before threading the catheter, the method may include twisting the cover, which may twist to the catheter hub to break adhesion between the introducer needle and the catheter.

It is to be understood that both the foregoing general description and the following detailed description are examples and explanatory and are not restrictive. It should be understood that the various embodiments are not limited to the arrangements and instrumentality shown in the drawings. It should also be understood that the embodiments may be combined, or that other embodiments may be utilized and that structural changes, unless so claimed, may be made without departing from the scope of the various embodiments of the present disclosure. The following detailed description is, therefore, not to be taken in a limiting sense.

BRIEF DESCRIPTION OF THE SEVERAL VIEWS OF THE DRAWINGS

Example embodiments will be described and explained with additional specificity and detail through the use of the accompanying drawings in which:

FIG. 1A is an upper perspective view of an example catheter system, illustrating the catheter system in an insertion configuration and an example cover, according to some embodiments;

FIG. 1B is an upper perspective view of the catheter system, illustrating an example catheter partially threaded off an example introducer needle, according to some embodiments;

FIG. 2A is an upper perspective view of the cover of FIG. 1A, illustrating a proximal end of the cover of FIG. 1A with an example extension removed, according to some embodiments;

FIG. 2B is an upper perspective view of the cover of FIG. 1A, illustrating a distal end of the cover of FIG. 1A with the extension removed, according to some embodiments;

FIG. 3A is an upper perspective view of the catheter system, illustrating another example cover and the catheter system in the insertion configuration, according to some embodiments;

FIG. 3B is an upper perspective view of the catheter system, illustrating the cover of FIG. 3A and the catheter partially threaded off the introducer needle, according to some embodiments;

FIG. 4A is an upper perspective view of the catheter system, illustrating another example cover and the catheter system in the insertion configuration, according to some embodiments;

FIG. 4B is an upper perspective view of the catheter system, illustrating the cover of FIG. 4A and the catheter partially threaded off the introducer needle, according to some embodiments;

FIG. 7A is a side view of the catheter system, illustrating an example cover and the catheter system in the insertion configuration, according to some embodiments; and FIG. 7B is a side view of the catheter system of FIG. 7A, illustrating the cover of FIG. 7A and the catheter partially threaded off the introducer needle, according to some embodiments.

DETAILED DESCRIPTION

Figure 1C:
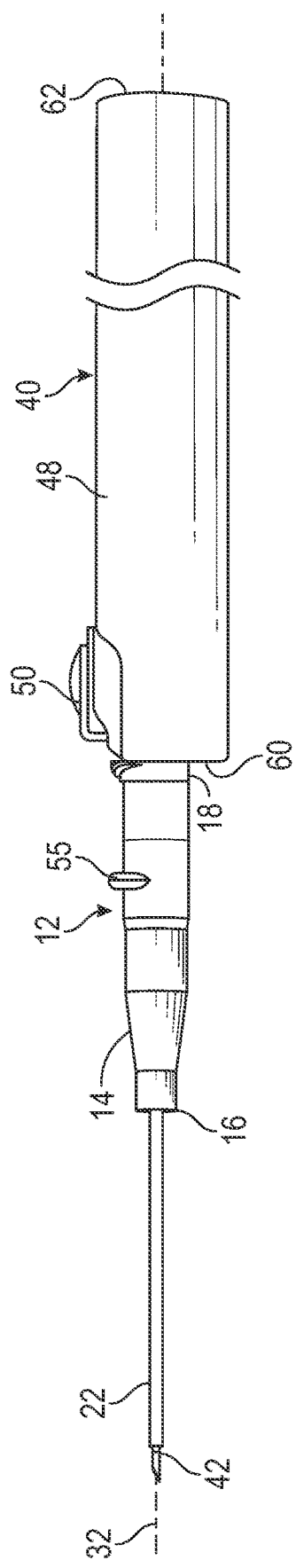
FIG. 1C is a side view of the catheter system in the insertion configuration with the cover of FIG. 1A and an example extension removed for illustration purposes, according to some embodiments.

Referring now to FIGS. 1A-1D, in some embodiments, a catheter system 10 may include a catheter assembly 12. In some embodiments, the catheter assembly 12 may include a catheter hub 14, which may include a distal end 16, a proximal end 18, and a lumen 20 extending through the distal end 16 of the catheter hub 14 and the proximal end 18 of the catheter hub 14. In some embodiments, the catheter assembly 12 may include a catheter 22 extending distally from the distal end 16 of the catheter hub 14. In some embodiments, the catheter 22 may be secured within the distal end 16 of the catheter hub 14. In some embodiments, the catheter 22 may include a peripheral intravenous catheter, a peripherally inserted central catheter, or a midline catheter.

In some embodiments, the catheter system 10 may include a cover 24, which may be coupled to a proximal portion 26 of the catheter hub 14. In some embodiments, the cover 24 may include a push tab 28 and/or a slot 30. In some embodiments, the push tab 28 may extend outwardly from a body of the cover 24. In some embodiments, the slot 30 may extend parallel to a longitudinal axis 32 of the catheter system 10. In some embodiments, the catheter system 10 may include an extension 34, which may include a distal end 36 and a proximal end 38. In some embodiments, the distal end 36 of the extension 34 may be slidable with respect to the slot 30. In some embodiments, the proximal end 38 of the extension 34 may be coupled to the needle hub 52.

In some embodiments, a user may grip the cover 24 instead of the catheter hub 14 during insertion of the catheter 22 into vasculature of a patient, which may reduce a risk of bacterial contamination of the catheter 22 and/or hospital-acquired infection. In some embodiments, the cover 24 may facilitate "no-touch" insertion of the catheter 22 (insertion of the catheter 22 without touching of the catheter hub 14 by the user) or "reduced-touch" insertion of the catheter 22.

In some embodiments, the catheter system 10 may include a needle assembly 40, which may include an introducer needle 42. In some embodiments, the introducer needle 42 may include a distal tip 44 and a proximal end 46. In some embodiments, the needle assembly 40 may include a housing 48, which may include an active safety mechanism. In some embodiments, the active safety mechanism may include a button 50. In some embodiments, the needle assembly 40 may include a needle hub 52 disposed within the housing 48. In some embodiments, the proximal end 46 of the introducer needle 42 may be secured within the needle hub 52.

In some embodiments, the distal end 36 of the extension 34 may be coupled to the cover 24 in various ways. In some embodiments, the distal end 36 may include a tab 54, which may extend through the slot 30 and may include an outer portion with a greater diameter than the slot 30. In some embodiments, the tab 54 may be slidable with respect to the slot 30. In some embodiments, the proximal end 38 of the extension 34 may be coupled to the needle hub 52 in various ways. In some embodiments, the proximal end 38 may be secured within a wall of the needle hub 52. In some embodiments, the proximal end 38 may be embedded within the wall of the needle hub 52. In some embodiments, the proximal end 38 may be engaged in an interference fit with the wall of the needle hub 52 or another suitable fit. In some embodiments, the proximal end 38 may be coupled to the needle hub 52 via an adhesive, solvent, or another suitable means. In some embodiments, the extension 34 may extend proximally into a hole 56. In some embodiments, the proximal end 38 may include a larger diameter than the hole 56 such that the proximal end 38 is prevented from moving distal to the hole 56 and secured within the needle hub 52. As illustrated in FIGS. 1A-1D, in some embodiments, the extension 34 may be rigid.

Figure 1D:
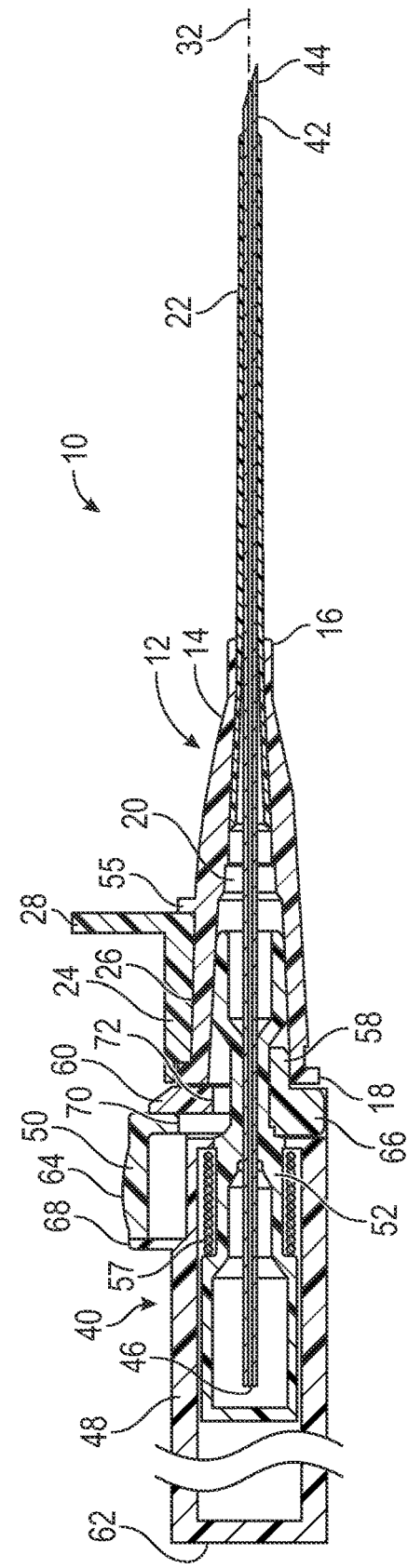
FIG. 1D is a cross-sectional view of the catheter system, illustrating the catheter system in the insertion configuration, according to some embodiments.

In some embodiments, in response to the catheter system 10 being in an insertion configuration, illustrated, for example, in FIGS. 1A and 1D, the catheter system 10 may be inserted into the vasculature of the patient. In some embodiments, the catheter hub 14 may include a push tab 55. In some embodiments, a distal end of the cover 24 may be proximate the push tab 55 when the catheter system 10 is in the insertion configuration. In some embodiments, in response to the introducer needle 42 and/or the catheter 22 being inserted into the vasculature, the catheter 22 may be partially threaded off the introducer needle 42, which may include contacting and applying a force in a distal direction to the cover 24 to advance the catheter 22 in the distal direction with respect to the introducer needle 42. FIG. 1B illustrates the catheter 22 partially threaded off the introducer needle 42, according to some embodiments. In some embodiments, in response to the catheter 22 being partially threaded off the introducer needle 42, the catheter 22 may be extended or threaded into the vasculature prior to the introducer needle 42 being retracted via the active safety mechanism. In some embodiments, threading the catheter 22 into the vasculature may increase a likelihood that the catheter 22 is properly placed within the vasculature.

In some embodiments, the housing 48 may include a barrel. In some embodiments, the active safety mechanism may include a spring 57 disposed within the housing 48 and a projection 58. In some embodiments, the button 50 may include or correspond to an activation latch. In some embodiments, the housing 48 may include a distal end 60 and a proximal end 62. In some embodiments, the needle hub 52 may be slidably disposed in the housing 48, which may be generally hollow. In some embodiments, the spring 57 may be disposed around the introducer needle 42 and/or between the needle hub 52 and the distal end 60 of the housing 48.

In some embodiments, the button 50 may include a top 64 and a bottom 66. In some embodiments, the button 50 may be movably mounted adjacent to the distal end 60 of the housing 48. In some embodiments, the button 50 may be adapted for selective engagement with the needle hub 52 to hold the needle hub 52 adjacent to the distal end 60 of the housing 48 against the bias of the spring 57 such that the introducer needle 42 extends beyond the distal end 60 of the housing 48 and through the catheter 22.

In some embodiments, the projection 58 may be disposed within the proximal end 18 of the catheter hub 14 to prevent movement of the button 50 when the catheter hub 14 is adjacent to the distal end 60 of the housing 48. In some embodiments, the projection 58 may be disposed adjacent the bottom 66 of the button 50. In some embodiments, the projection 58 may extend from the button 50 for engagement with the catheter hub 14 to prevent movement of the button 50 when the catheter hub 14 is adjacent to the distal end 60 of the housing 48, as illustrated, for example, in FIG. 1D. In some embodiments, the projection 58 may extend toward the distal end 16 of the catheter hub 14.

In some embodiments, the button 50 may extend into the housing 48 via a slot 68, which may be formed in the housing 48 adjacent to the distal end 60. In some embodiments, the button 50 may include an opening 70, and the distal end 60 of the housing 48 may include an opening 72. In some embodiments, the opening 70 and the opening 72 may allow the introducer needle 42 and the needle hub 52 to extend through the button 50 and the distal end 60 of the housing 48. In some embodiments, when the button 50 is "up" in a non-activated position, as illustrated, for example, in FIG. 1D, the projection 58 may engage the needle hub 52 and hold the needle hub 52 adjacent to the distal end 60 of the housing 48 against the force of the spring 57. In some embodiments, the needle hub 52 may include a generally hour-glass shape so that its medial portion has a smaller diameter than either end. This shape may facilitate engagement between the projection 58 and the needle hub 52.

In some embodiments, when the button 50 is in the non-activated position, the projection 58 may be located inside the catheter hub 14. Thus, when the catheter system 10 is in the insertion configuration and the introducer needle 42 extends through the catheter 22, the projection 58 may prevent the button 50 from being moved "down" into an activated position.

In some embodiments, a length of the projection 58 may vary. In some embodiments, a length of the projection 58 may be long enough so the projection 58 engages the catheter hub 14 when the catheter hub 14 is adjacent to the distal end 60 of the housing 48. In some embodiments, the length of the projection 58 may not be so long that it interferes with use of the catheter 22 and the introducer needle 42. In some embodiments, the active safety mechanism may be described further in U.S. Pat. No. 5,501,675, which is hereby incorporated by reference in its entirety.

In some embodiments, in response to the catheter 22 being partially threaded off the introducer needle 42 by advancing the catheter 22 distally with respect to the introducer needle 42, the catheter hub 14 may not be adjacent to the distal end 60 of the housing 48. In these and other embodiments, the button 50 can be moved "down," i.e. activated, because the catheter hub 14 no longer interferes with the movement of the projection 58. In this position, the projection 58 may no longer engage the needle hub 52. In some embodiments, when the button 50 is activated, a diameter of the opening 72 may increase. In some embodiments, when the button 50 is activated, the opening 70 and the opening 72 may be larger than a maximum diameter of the needle hub 52. In some embodiments, the spring 57 can thus force the needle hub 52 to the proximal end 62 of the housing 48 and withdraw the distal tip 44 of the introducer needle 42 into the housing 48, shielding the distal tip 44 and protecting the user and/or the patient from an accidental needle stick.

FIG. 1B illustrates distal advancement of the catheter hub 14 and the catheter 22 with respect to housing 48 prior to activation of the button 50, according to some embodiments. In some embodiments, as illustrated, for example, in FIG. 1B, the user may distally advance the catheter hub 14 and the catheter 22 or partially thread the catheter 22 off the introducer needle 42 after the user observes blood flashback. In some embodiments, the user may contact or grip the cover but not the catheter hub 14 to distally advance the catheter hub 14 and the catheter 22. In some embodiments, after the catheter hub 14 is distally advanced, the user may depress the button 50, which may retract the introducer needle 42 into the housing 48. In some embodiments, in response to activation of the button 50, the cover 24 may be pulled proximally and removed from the proximal portion 26 of the catheter hub 14. In some embodiments, before partially threading the catheter 22 off the introducer needle 42 and the distal advancement of the catheter hub 14 and the catheter 22, the user may twist the cover 24, which may twist the catheter hub 14 to break adhesion between the introducer needle 42 and the catheter 22.

Referring now to FIGS. 2A-2B, in some embodiments, the extension 34 may extend through an opening 74 in a proximal end of the cover 24.

Referring now to FIGS. 3A-3B, a cover 76 is illustrated, according to some embodiments. In some embodiments, the cover 76 may be similar or identical to the cover 24 of FIGS. 1A-2B in terms of one or more features and/or operation. in some embodiments, the cover 76 may include a proximal extension 78 covering at least a portion of the button 50 when the catheter system 10 is in the insertion configuration to prevent premature activation of the button 50. In some embodiments, the proximal extension 78 may extend from a proximal end of the cover 76.

Referring now to FIGS. 4A-4B, a cover 80 is illustrated, according to some embodiments. In some embodiments, the cover 80 may be similar or identical to the cover 24 of FIGS. 1A-2B and/or the cover 76 of FIGS. 3A-3B in terms of one or more features and/or operation. In some embodiments, a distal end of the cover 80 may include an arm 82, which may extend distally along a side of the catheter hub 14. In some embodiments, the arm 82 may include at least a portion of the slot 30.

Figure 5A:
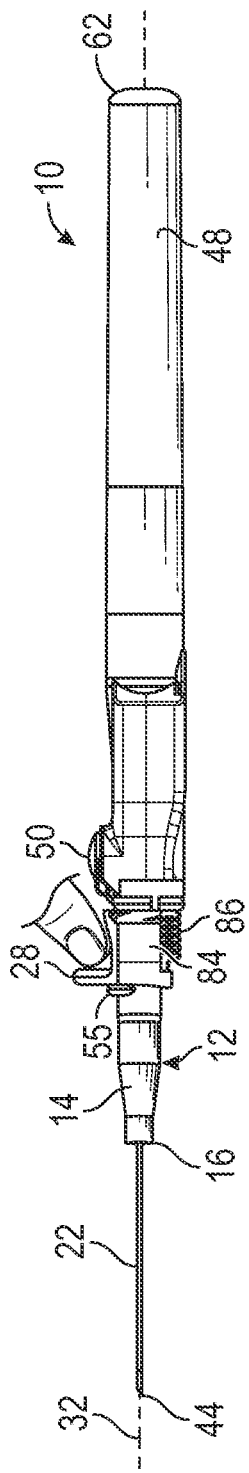
FIG. 5A is a side view of the catheter system, illustrating another example cover and another example extension, and the catheter system in the insertion configuration, according to some embodiments.
Figure 5B:
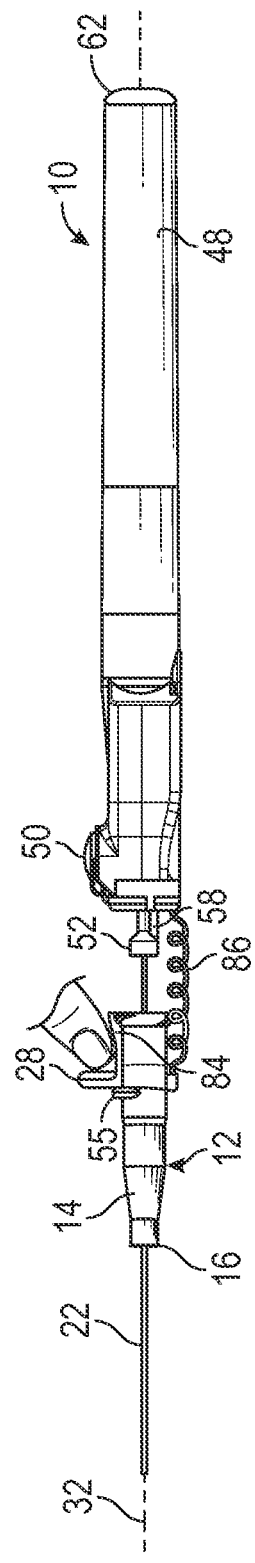
FIG. 5B is a side view of the catheter system, illustrating the cover and the extension of FIG. 5A and the catheter partially threaded off the introducer needle, according to some embodiments.
Figure 5C:
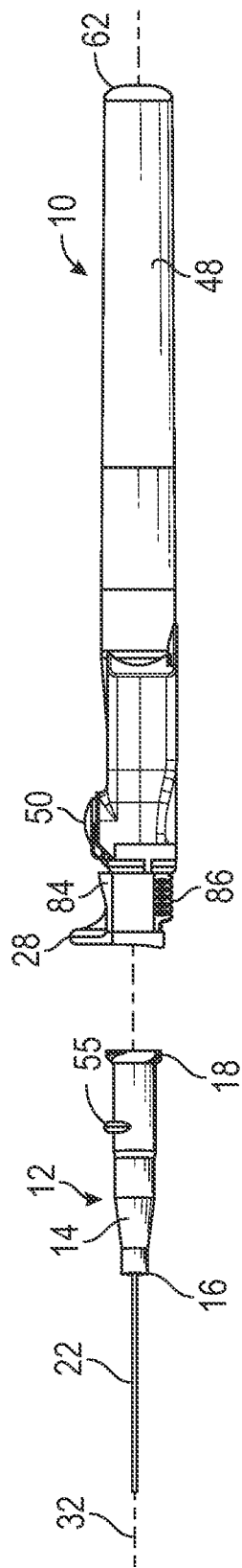
FIG. 5C is a side view of the catheter system, illustrating the cover and the extension of FIG. 5A proximate an example housing and shielding a distal tip of the introducer needle.

Referring now to FIGS. 5A-5C, a cover 84 and an extension 86 are illustrated, according to some embodiments. In some embodiments, the cover 84 may be similar or identical to one or more of the following in terms of one or more features and/or operation: the cover 24 of FIGS. 1A-2B, the cover 76 of FIGS. 3A-3B, and the cover 80 of FIGS. 4A-4B. In some embodiments, the extension 86 may be similar or identical to the extension 34 of FIGS. 1A-4B. In some embodiments, the extension 86 may include a spring. In some embodiments, a proximal end of the extension 86 may be coupled to the housing 48 and a distal end of the extension 86 may be coupled to the cover 84.

In some embodiments, in response to activation of the button 50, the needle hub 52 may move proximally within the housing 48 and a portion of the introducer needle 42 may be disposed within the housing 48. In some embodiments, in response to activation of the button 50, the needle hub 52 may move proximally within the housing 48, and the distal tip 44 of the introducer needle 42 may be distal to the housing 48. In some embodiments, in response to release of the cover 84 by the user, the spring may contract, and the cover 84 may move proximate the housing 48 and shield the distal tip 44 of the introducer needle 42. In these and other embodiments, the barrel may be shortened.

Figure 6A:
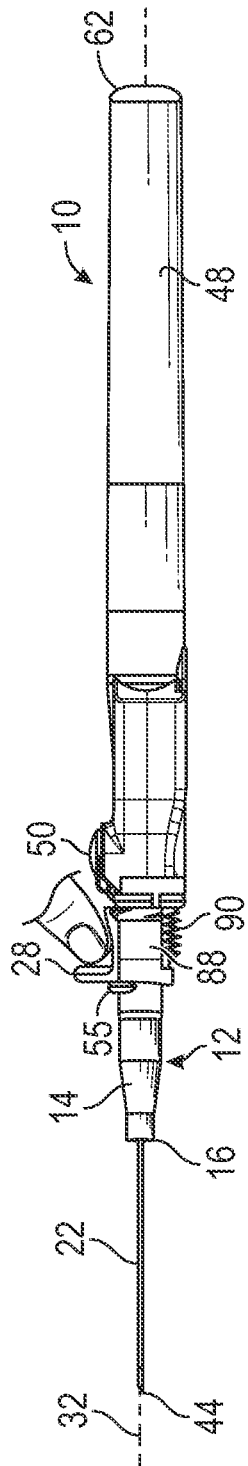
FIG. 6A is a side view of the catheter system, illustrating another example cover and another example extension, and the catheter system in the insertion configuration, according to some embodiments.
Figure 6B:
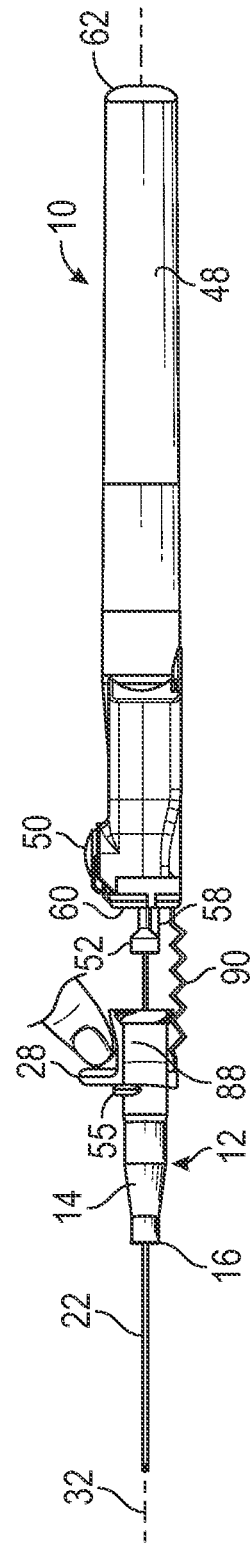
FIG. 6B is a side view of the catheter system, illustrating the cover and the extension of FIG. 6A and the catheter partially threaded off the introducer needle, according to some embodiments.
Figure 6C:
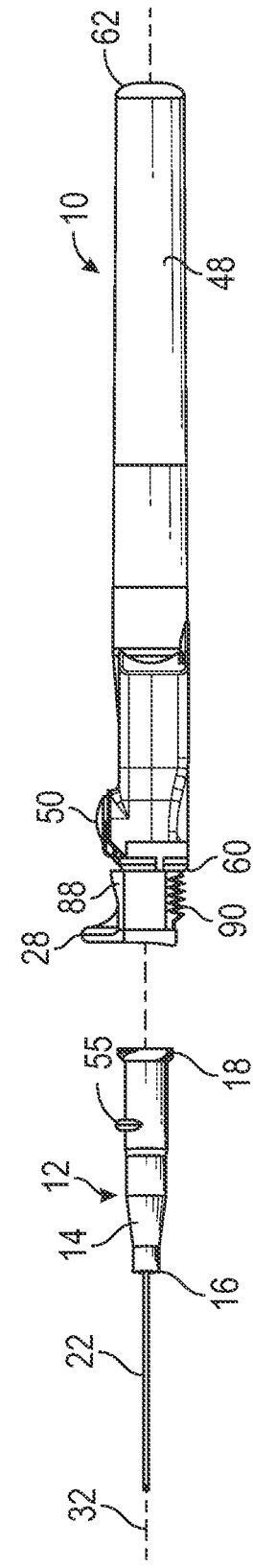
FIG. 6C is a side view of the catheter system, illustrating the cover and the extension of FIG. 6A proximate an example housing and shielding a distal tip of the introducer needle.

Referring now to FIGS. 6A-6B, a cover 88 and an extension 90 are illustrated, according to some embodiments. In some embodiments, the cover 88 may be similar or identical to one or more of the following in terms of one or more features and/or operation: the cover 24 of FIGS. 1A-2B, the cover 76 of FIGS. 3A-3B, the cover 80 of FIGS. 4A-4B, and the cover 84 of FIGS. 5A-5C. In some embodiments, the extension 86 may be similar or identical to the extension 90 of FIGS. 1A-4B and/or the extension 86 of FIGS. 5A-5C. In some embodiments, the extension 90 may include a tether. In some embodiments, the tether may include any suitable tether. In some embodiments, the tether may fold in an accordion-like fashion.

Referring now to FIGS. 7A-7B, in some embodiments, an outer surface of a cover 92 may include one or more protrusions 94 to facilitate gripping of the cover 92 by a user. In these and other embodiments, the user may manually remove the cover 92 after partially threading the catheter 22 off the introducer needle 42 and threading the catheter 22 into the vasculature. In some embodiments, the cover 92 may be similar or identical to one or more of the following in terms of one or more features and/or operation: the cover 24 of FIGS. 1A-2B, the cover 76 of FIGS. 3A-3B, the cover 80 of FIGS. 4A-4B, the cover 84 of FIGS. 5A-5C, and the cover 88 of FIGS. 6A-6B.

All examples and conditional language recited herein are intended for pedagogical objects to aid the reader in understanding the present disclosure and the concepts contributed by the inventor to furthering the art, and are to be construed as being without limitation to such specifically recited examples and conditions. Although embodiments of the present disclosure have been described in detail, it should be understood that the various changes, substitutions, and alterations could be made hereto without departing from the spirit and scope of the present disclosure.

I claim:
1. A catheter system, comprising:
 a catheter assembly, comprising:
  a catheter hub, comprising a distal end, a proximal end, and a lumen extending through the distal end of the catheter hub and the proximal end of the catheter hub; and
  a catheter extending distally from the distal end of the catheter hub;
 a needle assembly, comprising:
  an introducer needle, comprising a distal tip and a proximal end;
  a housing, comprising a button; and
  a needle hub disposed within the housing, wherein the proximal end of the introducer needle is secured within the needle hub; wherein in response to an activation of the button, the needle hub and the introducer needle move proximally within the housing;
 a cover coupled to a proximal portion of the catheter hub, wherein the cover comprises a push tab and a slot, wherein the slot extends parallel to a longitudinal axis of the catheter system aligned with the introducer needle; and
 an extension, comprising a distal end and a proximal end, wherein the distal end of the extension is disposed within the slot and slidable within the slot, wherein the proximal end of the extension is coupled the needle hub.

2. The catheter system of claim 1, wherein in response to the activation of the button, the cover is pulled proximally and removed from the proximal portion of the catheter hub.

3. The catheter system of claim 1, wherein the extension comprises a tether.

4. The catheter system of claim 1, wherein the extension comprises a spring.

5. The catheter system of claim 1, wherein the extension is rigid.

6. The catheter system of claim 1, wherein the cover comprises a proximal extension covering at least a portion of the button to prevent premature activation of the button.

7. The catheter system of claim 1, wherein the catheter hub comprises a push tab, wherein a distal end of the cover is proximate the push tab of the catheter hub.

8. The catheter system of claim 1, wherein a distal end of the cover comprises an arm extending distally along a side of the catheter hub, wherein the arm comprises a portion of the slot.

9. The catheter system of claim 8, wherein the catheter hub comprises a push tab, wherein the arm extends distal to the push tab of the catheter hub.

10. A catheter system, comprising:
a catheter assembly, comprising:
a catheter hub, comprising a distal end, a proximal end, and a lumen extending through the distal end of the catheter hub and the proximal end of the catheter hub; and
a catheter extending distally from the distal end of the catheter hub; and
a needle assembly, comprising:
an introducer needle, comprising a distal tip and a proximal end;
a housing, comprising a button; and
a needle hub disposed within the housing, wherein the proximal end of the introducer needle is secured within the needle hub; wherein in response to an activation of the button, the needle hub and the introducer needle move proximally within the housing;
a cover coupled to a proximal portion of the catheter hub, wherein the cover comprises a push tab; and
an extension, wherein the extension comprises a distal end and a proximal end, wherein the distal end of the extension is coupled to the cover, wherein the proximal end of the extension is coupled to the needle hub, wherein the extension comprises a spring, wherein in response to the activation of the button, the needle hub moves proximally within the housing and a portion of the introducer needle is disposed within the housing, wherein in response to release of the cover by a user, the spring contracts and the cover moves proximate the housing and shields the distal tip of the introducer needle.

11. The catheter system of claim 10, wherein the cover comprises a proximal extension covering at least a portion of the button to prevent premature activation of the button.

12. The catheter system of claim 10, wherein an outer surface of the cover comprises a plurality of protrusions to facilitate gripping of the cover by a user.

13. A method to reduce contact with a catheter assembly, comprising:
inserting a catheter system into vasculature of a patient, wherein the catheter system comprises:
the catheter assembly, comprising:
a catheter hub, comprising a distal end, a proximal end, and a lumen extending through the distal end of the catheter hub and the proximal end of the catheter hub; and
a catheter extending distally from the distal end of the catheter hub;
a needle assembly, comprising:
an introducer needle, comprising a distal tip and a proximal end,
a housing, comprising a button; and
a needle hub disposed within the housing, wherein the proximal end of the introducer needle is secured within the needle hub; wherein in response to an activation of the button, the needle hub and the introducer needle move proximally within the housing;
a cover coupled to a proximal portion of the catheter hub, wherein the cover comprises a push tab and a slot, wherein the slot extends parallel to a longitudinal axis of the catheter system aligned with the introducer needle; and
an extension comprising a distal end and a proximal end, wherein a distal end of the extension is disposed within the slot, wherein the proximal end of the extension is coupled to the needle hub; and
threading the catheter, comprising contacting and applying a force in a distal direction to the cover to advance the catheter in the distal direction with respect to the introducer needle,
wherein the distal end of the extension slides within the slot in response to threading the catheter.

14. The method of claim 13, further comprising activating the button after threading the catheter, wherein in response to the activation of the button, the cover is removed from the proximal portion of the catheter hub.

15. The method of claim 14, wherein the extension comprises a tether or a spring.

16. The method of claim 14, wherein the extension is rigid.

17. The method of claim 13, wherein the extension comprises a spring, wherein in response to the activation of the button, a portion of the introducer needle is disposed within the housing, further comprising releasing the cover, wherein in response to the releasing of the cover, the cover moves proximate the housing and shields the distal tip of the introducer needle.

18. The method of claim 13, further comprising, before threading the catheter, twisting the cover to break adhesion between the introducer needle and the catheter.

* * * * *